United States Patent
Park et al.

(10) Patent No.: US 11,756,207 B2
(45) Date of Patent: Sep. 12, 2023

(54) APPARATUS AND METHOD FOR LESION ANALYSIS BASED ON MARGINAL FEATURE

(71) Applicants: Research & Business Foundation Sungkyunkwan University, Suwon-si (KR); SAMSUNG LIFE PUBLIC WELFARE FOUNDATION, Seoul (KR)

(72) Inventors: Hyunjin Park, Suwon-si (KR); Hwanho Cho, Suwon-si (KR); Ho Yun Lee, Seoul (KR)

(73) Assignees: Research & Business Foundation Sungkyunkwan University, Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 247 days.

(21) Appl. No.: 17/332,380

(22) Filed: May 27, 2021

(65) Prior Publication Data

US 2022/0067945 A1 Mar. 3, 2022

(30) Foreign Application Priority Data

Sep. 1, 2020 (KR) .................. 10-2020-0110864

(51) Int. Cl.
*G06T 7/13* (2017.01)
*G06T 7/11* (2017.01)
(Continued)

(52) U.S. Cl.
CPC ............... *G06T 7/13* (2017.01); *A61B 6/032* (2013.01); *G06T 7/11* (2017.01); *G06T 7/40* (2013.01);
(Continued)

(58) Field of Classification Search
CPC ....................................................... G06T 7/13
See application file for complete search history.

(56) References Cited

U.S. PATENT DOCUMENTS

| | | | |
|---|---|---|---|
| 7,899,514 B1 * | 3/2011 | Kirkland | G06T 7/0012 600/407 |
| 2008/0205717 A1 * | 8/2008 | Reeves | G06T 5/002 382/128 |

(Continued)

FOREIGN PATENT DOCUMENTS

| | | |
|---|---|---|
| JP | 2002-517836 A | 6/2002 |
| KR | 10-1414413 B1 | 7/2014 |
| KR | 10-1927481 B1 | 12/2018 |

OTHER PUBLICATIONS

Korean Office Action dated Jan. 25, 2022 in counterpart Korean Patent Application No. 10-2020-0110864 (5 pages in Korean).

*Primary Examiner* — Oneal R Mistry
(74) *Attorney, Agent, or Firm* — NSIP Law (57) ABSTRACT

Disclosed are an apparatus and a method for lesion analysis based on a marginal feature. The method for lesion analysis based on a marginal feature according to an embodiment of the present disclosure may include receiving image data for a target region, identifying a lesion region from the image data, deriving a marginal feature for a lesion based on intensity information of the identified lesion region, and inferring an attribute associated with the lesion based on the marginal feature.

13 Claims, 6 Drawing Sheets

(51) Int. Cl.
*G06T 7/40* (2017.01)
*A61B 6/03* (2006.01)
(52) U.S. Cl.
CPC .............. *G06T 2207/10081* (2013.01); *G06T 2207/30061* (2013.01); *G06T 2207/30096* (2013.01)

(56) References Cited

U.S. PATENT DOCUMENTS

| | | | |
|---|---|---|---|
| 2014/0064449 A1* | 3/2014 | Deng | A61B 6/4441 378/62 |
| 2018/0070905 A1* | 3/2018 | El-Baz | G06T 7/149 |
| 2019/0183444 A1* | 6/2019 | Castillo | A61B 6/5235 |
| 2022/0076410 A1* | 3/2022 | Georgescu | G06N 3/08 |

* cited by examiner

| | | |
|---|---|---|
| Autocorrelation | $\text{Autocorrelation} = \sum_{i=1}^{N_g} \sum_{j=1}^{N_g} ijP(i,j)$ | Measures of the magnitude of the fineness and |
| Cluster tendency | $\text{Cluster tendency} = \sum_{i=1}^{N_g} \sum_{j=1}^{N_g} [i+j-\mu_x-\mu_y]^2 P(i,j)$ | Measures of the homogeneity of GLCM |
| Maximum probability | $\text{Maximum probability} = \max\{P(i,j)\}$ | Measures maximum value of GLCM matrix |
| Contrast | $\text{Contrast} = \sum_{i=1}^{N_g} \sum_{j=1}^{N_g} |i-j|^2 P(i,j)$ | Measures of the local intensity variation of GLCM |
| Difference entropy | $\text{Difference entropy} = \sum_{i=0}^{N_g-1} P_{x-y}(i) \log_2 [P_{x-y}(i)]$ | Measures entropy of processed GLCM matrix Px-y |
| Dissimilartiy | $\text{Dissimilartiy} = \sum_{i=1}^{N_g} \sum_{j=1}^{N_g} |i-j|P(i,j)$ | Measures differences of entries in GLCM |
| Energy | $\text{Energy} = \sum_{i=1}^{N_g} \sum_{j=1}^{N_g} [P(i,j)]^2$ | Measures of the homogeneity of GLCM |
| Entropy | $\text{Entropy} = -\sum_{i=1}^{N_g} \sum_{j=1}^{N_g} P(i,j) \log_2[P(i,j)]$ | Measures irregularity of GLCM |
| Homogeneity1 | $\text{Homogeneity1} = \sum_{i=1}^{N_g} \sum_{j=1}^{N_g} \frac{P(i,j)}{1+|i-j|}$ | Measures closeness of GLCM |
| Informational measure of correlation 1 (IMC1) | $\text{IMC1} = \frac{HXY - HXY1}{\max\{HX,HY\}}$ | Secondary measures of Homogeneity1 |
| Variance | $\text{Variance} = \sum_{i=1}^{N_g} \sum_{j=1}^{N_g} (i-\mu_x)^2 P(i,j)$ | Measures dispersion of the parameter values around the mean of the combinations of reference and neighborhood pixels |
| Sum average | $\text{Sum average} = \sum_{i=2}^{2N_g} [iP_{x-y}(i)]$ | |
| Sum entropy | $\text{Sum entropy} = -\sum_{i=2}^{2N_g} P_{x-y}(i) \log_2[P(i)]$ | |
| Sum variance | $\text{Sum variance} = \sum_{i=2}^{2N_g} (i-SA)^2 P_{x-y}(i)$ | |
| Inverse variance | $\text{Inverse variance} = \sum_{i=1}^{N_g} \sum_{j=1}^{N_g} \frac{P(i,j)}{|i-j|^2}, i \neq j$ | |
| Invese Difference Moment Normalized (IDMN) | $\text{IDMN} = \sum_{i=1}^{N_g} \sum_{j=1}^{N_g} \frac{P(i,j)}{1+\left(\frac{|i-j|^2}{N^2}\right)}$ | |

APPARATUS AND METHOD FOR LESION ANALYSIS BASED ON MARGINAL FEATURE

CROSS-REFERENCE TO RELATED APPLICATIONS

This application claims the priority of Korean Patent Application No. 10-2020-0110864 filed on Sep. 1, 2020, in the Korean Intellectual Property Office, the disclosure of which is incorporated herein by reference.

BACKGROUND

Field

The present disclosure relates to an apparatus and a method for lesion analysis based on a marginal feature. For example, the present disclosure relates to a technique for analyzing invasiveness of lung adenocarcinoma by quantifying a marginal region of a lung adenocarcinoma lesion showing a ground glass opacity feature from image data of a lung region and distinguishing various subtypes of the lung adenocarcinoma based thereon.

Description of the Related Art

Lung cancer is fatal cancer with a high mortality, and despite the development of technology for treating lung cancer, a five-year survival rate for all lung cancer patients remains low. On the other hand, since lung cancer diagnosed early has a very high cure rate, efforts to diagnose lung cancer early are very important in addition to prevention and treatment of lung cancer.

Particularly, the lung adenocarcinoma may be pathologically classified into adenocarcinoma in situ (AIS), minimally invasive adenocarcinoma (MIA), and invasive adenocarcinoma (IA) based on invasiveness of cancer according to a multidisciplinary classification of lung adenocarcinoma proposed in 2011. There is a difference in that the AIS and the MIA have a five-year disease-free survival (DFS) of nearly 100% after complete excision, while patient with stage 1 IA have the DFS of 74.6%. The DFS shows a tendency to decrease as an invasive tumor component increases. Further, with respect to specific treatment methods, in the AIS and the MIA, it may be considered to apply sublobar resection instead of lobectomy which is currently generally applied for excision of early lung cancer, and as such, treatment options may be differently applied depending on the diagnosis before surgery for the lung adenocarcinoma lesion.

That is, since a treatment method that may be applied to each subtype classification of the lung adenocarcinoma described above varies, if the subtype of lung adenocarcinoma may be distinguished early through the image data, such as lung CT, it is expected to be able to establish an effective treatment plan.

In this regard, in order to determine the invasiveness of lung adenocarcinoma or to classify the subtype of lung adenocarcinoma, in the related art, even in the case of adopting a method of invasively performing tissue biopsy or utilizing non-invasively image data, mainly, experts simply check and then determine visual information, such as the size and shape of tumor, or an expression form of a margin part shown in the image with the naked eye, so that the dependence on subjective judgment is only high. That is, no matter what the expert determines, since the subjectivity of the expert is eventually intervened, a manual decision-making method by the expert has a clear limitation in terms of reproducibility and rapidity for the subtype classification.

Further, in the related art, there have been many attempts for distinguishing the subtypes of lung adenocarcinoma, but in all of the AIS, the MIA, and the IA, generally, the ground glass nodule (GGN) is observed, and redundancies exist in many areas across a spectrum in the image, making it difficult to interpret radiology through the layering of the GGN.

The background art of the present disclosure is disclosed in Korean Patent Registration No. 10-1414413.

SUMMARY

An object to be achieved by the present disclosure is to provide an apparatus and a method for lesion analysis based on a marginal feature capable of deriving a marginal feature of a lesion region identified from image data and inferring an attribute associated with the corresponding lesion based on the derived marginal feature.

Further, another object to be achieved by the present disclosure is to provide an apparatus and a method for lesion analysis based on a marginal feature capable of quantifying features of a margin part of a lung region lesion and distinguishing subtypes of lung adenocarcinoma based on an objective criteria.

Objects of the present disclosure are not limited to the above-mentioned objects, and other objects, which are not mentioned above, may be clearly understood by those skilled in the art from the following descriptions.

According to an aspect of the present disclosure, there is provided a method for lesion analysis based on a marginal feature including: receiving image data for a target region; identifying a lesion region from the image data; deriving a marginal feature for a lesion based on intensity information of the identified lesion region; and inferring an attribute associated with the lesion based on the marginal feature.

The deriving of the marginal feature may include acquiring maximum intensity and minimum intensity in the identified lesion region; calculating a cumulative distribution function (CDF) for the lesion region by setting intensity information between the minimum intensity and the maximum intensity as a threshold; and deriving the marginal feature based on the CDF.

The inferring of the attribute may be inferring invasiveness associated with the lesion as the attribute based on the marginal feature by reflecting an aspect that the CDF is rapidly changed or gently changed.

The deriving of the marginal feature based on the CDF may be deriving an average, a standard deviation, skewness, and kurtosis of slope values of the CDF as the marginal feature based on the graph of the CDF.

The lesion analysis method based on a marginal feature according to an embodiment of the present disclosure may further include classifying a type of the lesion based on the inferred attribute.

The target region may be lung and the type of the lesion may be classified based on the invasiveness of the lung region lesion.

The type of the lesion may include adenocarcinoma in situ, minimally invasive adenocarcinoma, and invasive adenocarcinoma.

The lesion analysis method based on a marginal feature according to an embodiment of the present disclosure may further include deriving a texture feature for an interior of a lesion based on the intensity information inside the lesion region, after the identifying of the lesion region.

The inferring of the attribute may be inferring the attribute associated with the lesion by considering both the marginal feature and the texture feature.

In addition, the image data may be 3D computed tomography (CT) data.

The lesion analysis method based on a marginal feature according to an embodiment of the present disclosure may further include searching a slice in which the lesion region is best identified among a plurality of 2D slices for the 3D CT data, after the receiving of the image data.

According to another aspect of the present disclosure, there is provided an apparatus for lesion analysis based on a marginal feature including: an image reception unit for receiving image data for a target region; an ROI detection unit for identifying a lesion region from the image data; a marginal feature calculation unit for deriving a marginal feature for a lesion based on intensity information of the identified lesion region; and a determination unit for inferring an attribute associated with the lesion based on the marginal feature.

The marginal feature calculation unit may include a CDF calculation unit for acquiring maximum intensity and minimum intensity in the identified lesion region and calculating a CDF for the lesion region by setting intensity information between the minimum intensity and the maximum intensity as a threshold; and a marginal feature calculation unit for deriving the marginal feature based on the CDF.

The determination unit may infer invasiveness associated with the lesion as the attribute based on the marginal feature by reflecting an aspect that the CDF is rapidly changed or gently changed.

The lesion analysis apparatus based on a marginal feature according to an embodiment of the present disclosure may further include an internal feature calculation unit for deriving a texture feature for an interior of a lesion based on the intensity information inside the lesion region.

The determination unit may infer the attribute associated with the lesion by considering both the marginal feature and the texture feature.

The target region may be lung, and the determination unit may classify a type of the lesion based on the inferred attribute and classify the type of the lesion based on the invasiveness of the lung region lesion.

The ROI detector may be configured to identify the lesion region based on identifying a ground glass opacity feature in the image data.

The ROI detector may be configured to identify the lesion region based on a set of pixels or a set of voxels exceeding a threshold intensity value from the image data.

The above-mentioned technical solutions are merely exemplary and should not be construed as limiting the present disclosure. In addition to the above-described exemplary embodiments, additional embodiments may exist in the drawings and detailed description of the invention.

According to the present disclosure, it is possible to provide an apparatus and a method for lesion analysis based on a marginal feature capable of deriving a marginal feature of a lesion region identified from image data and inferring an attribute associated with the corresponding lesion based on the derived marginal feature.

Further, according to the present disclosure, it is possible to provide an apparatus and a method for lesion analysis based on a marginal feature capable of quantifying features of a margin part of a lung region lesion and distinguishing subtypes of lung adenocarcinoma based on an objective criteria.

Further, according to the present disclosure, it is possible to solve a problem of subjectivity and rapidity of the determination which has been performed passively by existing experts by objectively and automatically quantifying information of the margin part of tumor with an image analysis technique.

Further, according to the present disclosure, it is possible to prevent a risk of additional infection that may be caused by an invasive method such as tissue biopsy and enable patient-specific personalized treatment based on a determining result by non-invasively determining an attribute of a lesion including subtypes and the like of lung adenocarcinoma.

The effects according to the present disclosure are not limited to the contents exemplified above, and more various effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which:

FIG. 3 is a table exemplarily illustrating a texture feature for an interior of a lesion acquisible from a gray level co-occurrence matrix (LLCM);

DETAILED DESCRIPTION OF THE EMBODIMENT

Hereinafter, embodiments of the present disclosure will be described in detail so as to be easily implemented by those skilled in the art, with reference to the accompanying drawings. However, the present disclosure may be embodied in many different forms and are not limited to the embodiments to be described herein. In addition, parts not related with the description have been omitted in order to clearly describe the present disclosure in the drawings and throughout this specification, like reference numerals designate like elements.

Further, throughout this specification, when a certain part is "connected" with the other part, it is meant that the certain part may be "directly connected" with the other part and "electrically connected" or "indirectly connected" with the other part with another element interposed therebetween.

Throughout this specification, it will be understood that when a certain member is located "on", "above", "at the top of", "under", "below", and "at the bottom of" the other member, a certain member is in contact with the other member and another member may also be present between the two members.

Throughout this specification, when a certain part "comprises" a certain component, unless otherwise disclosed to the contrary, it is meant that the part may further comprise another component without excluding another component.

The present disclosure relates to an apparatus and a method for lesion analysis based on a marginal feature. For example, the present disclosure relates to a technique for analyzing invasiveness of lung adenocarcinoma by quantifying a marginal region of a lung adenocarcinoma lesion showing a ground glass opacity feature from image data of a lung region and distinguishing various subtypes of the lung adenocarcinoma based thereon.

Figure 1:
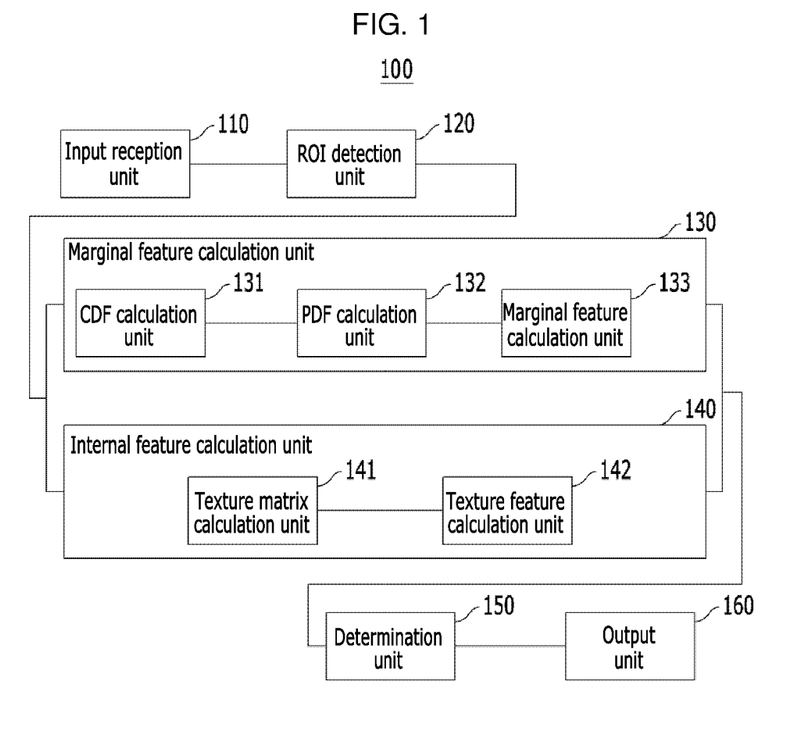
FIG. 1 is a schematic diagram of an apparatus for lesion analysis based on a marginal feature according to an embodiment of the present disclosure.

FIG. 1 is a schematic diagram of an apparatus for lesion analysis based on a marginal feature according to an embodiment of the present disclosure.

Referring to FIG. 1, an apparatus 100 for lesion analysis based on a marginal feature according to an embodiment of the present disclosure (hereinafter, referred to as a 'lesion analysis apparatus 100') may include an input reception unit 110, a region of interest (ROI) detection unit 120, a marginal feature calculation unit 130, an internal feature calculation unit 140, a determination unit 150, and an output unit 160.

Further, referring to FIG. 1, the marginal feature calculation unit 130 of the lesion analysis apparatus 100 may include a CDF calculation unit 131, a probability density function (PDF) calculation unit 132, and a marginal feature calculation unit 133. Further, referring to FIG. 1, the internal feature calculation unit 140 of the lesion analysis apparatus 100 may include a texture matrix calculation unit 141 and a texture feature calculation unit 142.

Although not illustrated, the lesion analysis apparatus 100 may receive image data to be analyzed from a photographing device (not illustrated) for photographing a medical image to a target region. Further, the lesion analysis apparatus 100 may provide a lesion analysis result for the image data received from the photographing device (not illustrated) to a user terminal (not illustrated) to allow the lesion analysis result to be output. As another example, the lesion analysis apparatus 100 disclosed herein may be provided in a form mounted in a software or module form in the photographing device (not illustrated).

More specifically, the photographing device (not illustrated) that provides the image data to the lesion analysis apparatus 100 may include, for example, a magnetic resonance imaging (MRI) scanner, a ultrasonic imaging device, a computed tomography (CT) device, a radiography device of X-rays, and the like. In addition, the image data to be analyzed by the lesion analysis apparatus 100 in response thereto may include an X-ray image, an MRI image, an ultrasonic image, a CT image, and the like.

The lesion analysis apparatus 100, the photographing device (not illustrated), and the user terminal (not illustrated) may communicate with each other via a network. The network means a connection structure in which information may be exchanged between nodes such as terminals and servers. Examples of the network include a 3rd generation partnership project (3GPP) network, a long term evolution (LTE) network, a 5G network, a world interoperability for microwave access (WIMAX) network, Internet, a local area network (LAN), a wireless local area network (Wireless LAN), a wide area network (WAN), a personal area network (PAN), a WiFi network, a Bluetooth network, a satellite broadcasting network, an analog broadcasting network, a digital multimedia broadcasting (DMB) network, and the like, but are not limited thereto.

The user terminal (not illustrated) may include, for example, a smartphone, a SmartPad, a tablet PC, etc., and all types of wireless communication devices, such as PCS (Personal Communication System), GSM (Global System for Mobile communication), PDC (Personal Digital Cellular), PHS (Personal Handyphone System), PDA (Personal Digital Assistant), IMT (International Mobile Telecommunication)-2000, CDMA (Code Division Multiple Access)-2000, W-CDMA (W-Code Division Multiple Access), and Wibro (Wireless Broadband Internet) terminal unit.

Hereinafter, the functions and operations of the lesion analysis apparatus 100 will be described in detail.

First, the input reception unit 110 of the lesion analysis apparatus 100 may receive image data for the target region. According to an embodiment of the present disclosure, the input reception unit 110 may receive the image data for the target region from the photographing device (not illustrated). Here, the target region may include lung of a subject. In addition, the image data may be 3D computed tomography (CT) data.

According to an embodiment of the present disclosure, when the received image data is the 3D CT data, the ROI detection unit 120 may search a slice in which a lesion region is best identified among a plurality of 2D slices for the 3D CT data. Here, the ROI detection unit 120 may identify the lesion region among the plurality of 2D slices and the slice to be searched to perform detailed analysis on the corresponding lesion may be determined as at least one number.

In this regard, exemplarily, it will be appreciated that the searching of the slice in which the lesion region is best identified by the ROI detection unit 120 is to select a 2D image in which a tumor (lesion) is largest expressed as a representative slice from the plurality of 2D slices generated based on a 3D lung CT and use the selected 2D image for a subsequent analysis process.

In addition, the ROI detection unit 120 may identify the lesion region from the received image data. According to an embodiment of the present disclosure, the ROI detection unit 120 may identify the lesion region from the searched slice in which the lesion region is best identified among the plurality of 2D slices.

According to an embodiment of the present disclosure, the ROI detection unit 120 may determine the lesion region to include a region where the ground glass opacity feature is shown in the image data in relation to lung adenocarcinoma.

Further, according to an embodiment of the present disclosure, the ROI detection unit 120 may determine a set of pixels or a set of voxels exceeding a predetermined threshold intensity value from the image data as a lesion region.

Further, according to an embodiment of the present disclosure, the ROI detection unit 120 may determine all tumor regions to be identified and included based on a reconstruction interval in the range of 1 to 2.5 mm from an upper portion to a lower portion of the tumor.

Further, the marginal feature calculation unit 130 may derive a marginal feature for the lesion based on intensity information of the identified lesion region.

Specifically, according to an embodiment of the present disclosure, the CDF calculation unit 131 may acquire maximum intensity and minimum intensity in the identified lesion region.

In addition, the CDF calculation unit 131 may calculate a CDF for a lesion region by setting intensity information between the acquired minimum intensity and maximum intensity as a threshold. Specifically, the CDF calculation unit 131 may sort a intensity value of each pixel forming the lesion region in ascending order from the minimum intensity value to the maximum intensity value and apply each sorted intensity value sequentially to the image data as the threshold to calculate a ratio of pixels lower than a set threshold as a CDF value for the corresponding threshold. In other words, the CDF calculation unit 131 may set each intensity value of each pixel forming the lesion region as a threshold and acquire a ratio of pixels in the lesion region showing the intensity value lower than the set threshold as a CDF value corresponding to the set threshold. Further, the CDF calculation unit 131 may generate a CDF graph by setting a threshold as a horizontal axis and a CDF value corresponding to the threshold as a vertical axis.

At this time, the graph of the generated CDF shows an upper-right feature (open form) in accordance with a probability theory, and the matters of the CDF are apparent to those skilled in the art, and thus, the detailed description will be omitted.

In addition, the marginal feature calculation unit 133 may derive the marginal feature based on the derived CDF.

According to an embodiment of the present disclosure, with regard with the marginal feature derived based on the CDF, the PDF calculation unit 132 may calculate a PDF of a slope value throughout an entire intensity value range (that is, a intensity information range between the minimum intensity and the maximum intensity) for the derived CDF. In addition, the marginal feature calculation unit 133 may acquire a slope feature according to a threshold change of the CDF from the derived PDF. Further, according to an embodiment of the present disclosure, the PDF calculation unit 132 may operate to calculate a slope of the CDF for each 5 hounsfield unit (HU) in an interval corresponding to a maximum value from a minimum value of the intensity value in the lesion region.

Specifically, according to an embodiment of the present disclosure, the marginal feature calculation unit 133 may derive an average, a standard deviation, skewness, and kurtosis of slope values of the CDF as the marginal feature in the graph of the CDF based on the PDF value derived for the CDF. That is, the marginal feature herein may be derived to reflect an aspect that the CDF is rapidly changed or gently changed in a margin of the lesion.

Further, the internal feature calculation unit 140 may derive a texture feature for the lesion inside based on intensity information inside the identified lesion region. In the description for the embodiment of the present disclosure, the texture feature for the lesion inside may mean intra-tumoral heterogeneity of a lesion (e.g., tumor).

Specifically, according to an embodiment of the present disclosure, the texture matrix calculation unit 141 may calculate a texture matrix corresponding to the lesion region (e.g., tumor region) acquired by the ROI detection unit 120. According to an embodiment of the present disclosure, the texture matrix calculation unit 141 may generate a texture matrix such as a gray-level co-occurrence matrix (LLCM), a gray-level size zone matrix (GLSZM), a neighbouring gray tone difference matrix (NGTDM), and the like.

Further, the texture feature calculation unit 142 may calculate high-order statistics information as a texture feature from the texture matrix acquired by the texture matrix calculation unit 141.

FIG. 3 is a table exemplarily illustrating a texture feature for an interior of a lesion acquisible from a gray level co-occurrence matrix (LLCM).

Referring to FIG. 3, the texture feature calculation unit 142 may acquire high-order statistics information such as autocorrelation, cluster tendency, maximum probability, contrast, difference entropy, dissimilarity, energy, entropy, and homogeneity as a texture feature from the gray level co-occurrence matrix (LLCM).

In addition, the determination unit 150 may infer an attribute associated with the lesion based on at least one of the marginal feature derived by the marginal feature calculation unit 130 and the texture feature derived by the internal feature calculation unit 140. More specifically, according to an embodiment of the present disclosure, the determination unit 150 may operate to infer an attribute associated with the lesion based on the marginal feature derived by the marginal feature calculation unit 130 or to infer an attribute associated with the lesion by considering both the marginal feature and the texture feature. In the description for the embodiment of the present disclosure, the attribute associated with the lesion may mean invasiveness associated with the lesion of cancer, tumor, or the like. In the description for the embodiment of the present disclosure, the 'invasiveness' may be referred to as intrusion, invasive degree, intrusion degree, intrusion force, and the like, and may mean a property in which cancer cells and the like in the lesion region may be invaded, bred, or transited to other regions in the body of a subject.

Hereinafter, referring to FIGS. 2A and 2B, it will be described that marginal features disclosed in the present disclosure are separately shown in a lesion with high invasiveness and a lesion with low invasiveness, respectively.

Figure 2A:
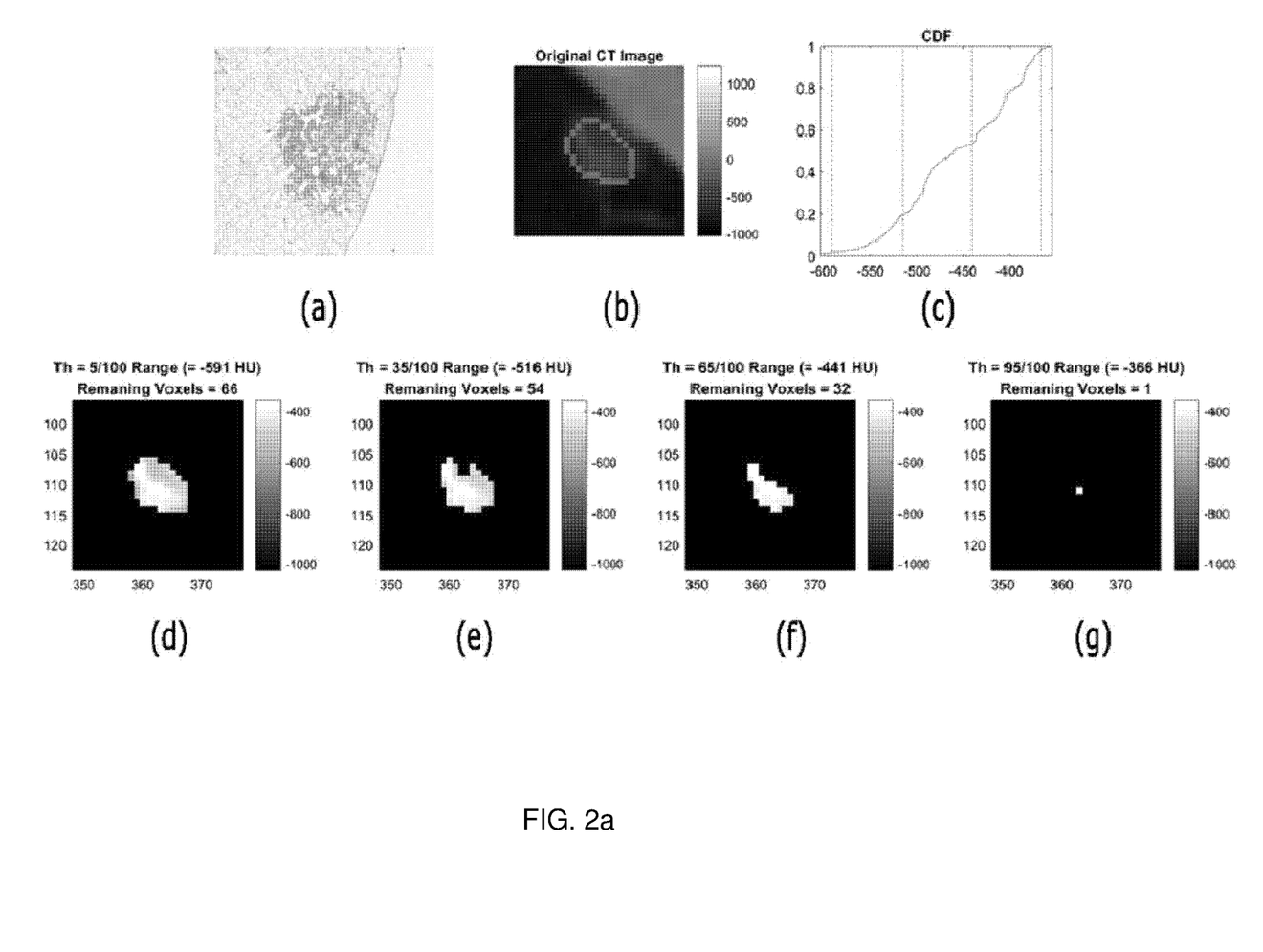
FIG. 2A is a diagram for describing a marginal feature shown in a lesion with high invasiveness.
Figure 2B:
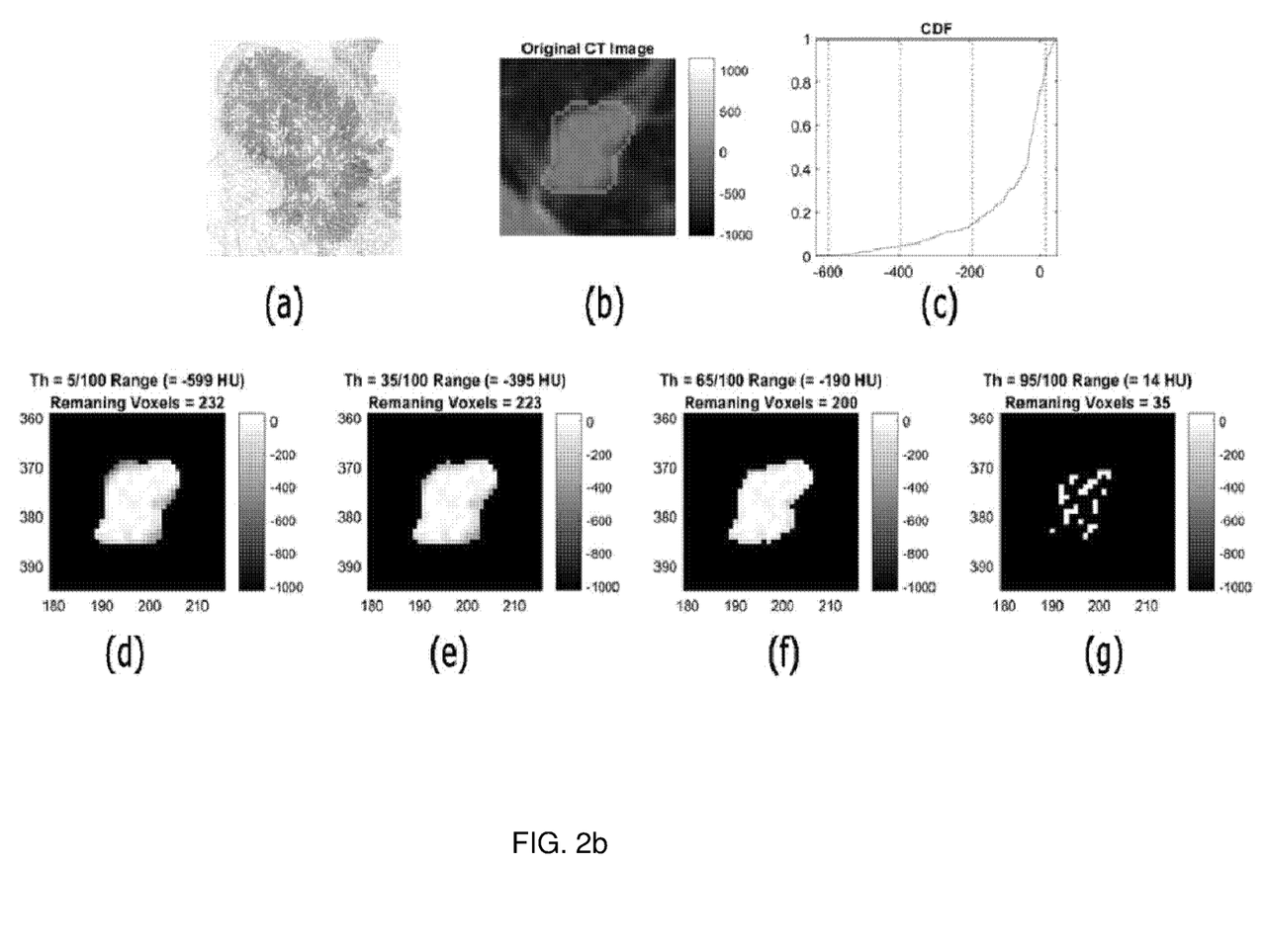
FIG. 2B is a diagram for describing a marginal feature shown in a lesion with low invasiveness.

FIG. 2A is a diagram for describing a marginal feature shown in a lesion with high invasiveness and FIG. 2B is a diagram for describing a marginal feature shown in a lesion with low invasiveness.

Specifically, FIG. 2A (a) illustrates a histolopathologic image when invasiveness of cancer is high, FIG. 2A (b) illustrates original CT image data in which a lesion region as a region of interest (ROI) is represented in green, FIGS. 2A (d) to (g) illustrate applying intensity information between maximum intensity and minimum intensity in the lesion region to image data as a threshold "Th", respectively, and FIG. 2A (c) is a graph of CDF derived based on a ratio of pixels lower than a threshold when each threshold is applied.

Further, FIG. 2B (a) illustrates a histolopathologic image when invasiveness of cancer is low, FIG. 2B (b) illustrates original CT image data in which a lesion region as a region of interest (ROI) is represented in green, FIGS. 2B (d) to (g) illustrate applying intensity information between maximum intensity and minimum intensity in the lesion region to image data as a threshold "Th", respectively, and FIG. 2B (c) is a graph of CDF derived based on a ratio of pixels lower than a threshold when each threshold is applied.

As compared with FIGS. 2A (c) and 2B (c), it may be confirmed that an open form of the CDF graph for the lesion (FIG. 2A) with high invasiveness has a relatively gentle form, but an open form of the CDF graph for the lesion (FIG. 2B) with low invasiveness is rapidly changed. In other words, with respect to the invasiveness of the lesion, a slope of the CDF graph that reflects a change in intensity feature in a marginal region of the lesion is gently shown when the invasiveness is high and rapidly shown when the invasiveness is low.

Further, in this regard, according to an embodiment of the present disclosure, a feature that the marginal feature is rapidly changed in the margin of the lesion may be described as the margin of the lesion is well-defined. On the contrary, a feature that the marginal feature is gently changed in the margin of the lesion may be described as the margin of the lesion is ill-defined. In other words, it will be understood that the marginal feature for the lesion with high invasiveness is ill-defined and the marginal feature for the lesion with low invasiveness is well-defined.

That is, the present disclosure is to be derived in that a subtype with low invasiveness of cancer is well-defined in a marginal region of the tumor as compared with other cell tissues and a subtype with high invasiveness of cancer is ill-defined in the marginal region of the tumor. The definement of the tumor margin part is modeled by using the CDF based on a probability theory by calculating a CDF value through many thresholds in a intensity value of a tumor region (lesion region) image to extract a unique image feature having a close relationship with the definement of the tumor margin part or the invasiveness of cancer.

Further, the determination unit 150 may classify a type of lesion on the basis of the attribute for the lesion inferred based on at least one of the marginal feature and the texture feature. Specifically, the determination unit 150 may classify the type of lesion based on the invasiveness of a lung region lesion if a target region is lung.

With respect to the type of lesion, according to an embodiment of the present disclosure, the type of lung region lesion may include adenocarcinoma in situ, minimally invasive adenocarcinoma, and invasive adenocarcinoma.

Further, according to an embodiment of the present disclosure, when feature information on the lesion such as the marginal feature, the texture feature, etc. is input, the determination unit 150 may evaluate the invasiveness for the corresponding lesion, and hold an artificial intelligence-based classification model learned to classify a subtype of lung adenocarcinoma based on the invasiveness evaluating result.

In other words, the determination unit 150 may include a classification model which learns invasiveness labeled on each lesion (tumor) by using feature values (e.g., marginal feature, texture feature, etc.) acquired from the marginal feature calculation unit 130 and the internal feature calculation unit 140. In this regard, according to an embodiment of the present disclosure, as the method for learning the classification model, a support vector machine (SVM), a random forest, an artificial neural network, etc. may be used. Particularly, in the case of the artificial neural network, a convolutional neural network (CNN) capable of extracting an abstraction feature from an image may be used. However, the present disclosure is not limited thereto, but in the present disclosure, various artificial intelligence-based algorithm models that are already known in the related art or to be developed in the future may be applied.

According to an embodiment of the present disclosure, the classification model held by the determination unit 150 may be learned by selecting a significant feature value and using the selected feature value in the prediction of invasiveness of the marginal feature or the texture feature through a logistic-LASSO process. Specifically, the classification model of the determination unit 150 may operate to hold a coefficient corresponding to the selected feature value above as a learning result to calculate the invasiveness of the lesion and infer the invasiveness of the lesion determined from the corresponding image data based on the held coefficient when a feature value for new image data is input.

The output unit 160 may present to identify information (e.g., invasiveness rank, subtype of lung adenocarcinoma, etc.) on the invasiveness derived from the determination unit 150 and features based on the invasiveness or the classification of the subtype of lung adenocarcinoma. According to an embodiment of the present disclosure, the output unit 160 may visualize and provide a determination basis region through a Grad-cam method when the determination unit 150 uses the artificial neural network. Here, according to an embodiment of the present disclosure, the visualizing and providing of the determination basis region may mean that a subject (medical staff, etc.) confirming an output result with the naked eye intuitively recognizes the determination basis region by comparing color, contrast, sharpness, etc. of the derived determination basis region with those of other regions of the image data.

Hereinafter, an operational flow of the present disclosure will be briefly described based on the contents described above in detail.

Figure 4:
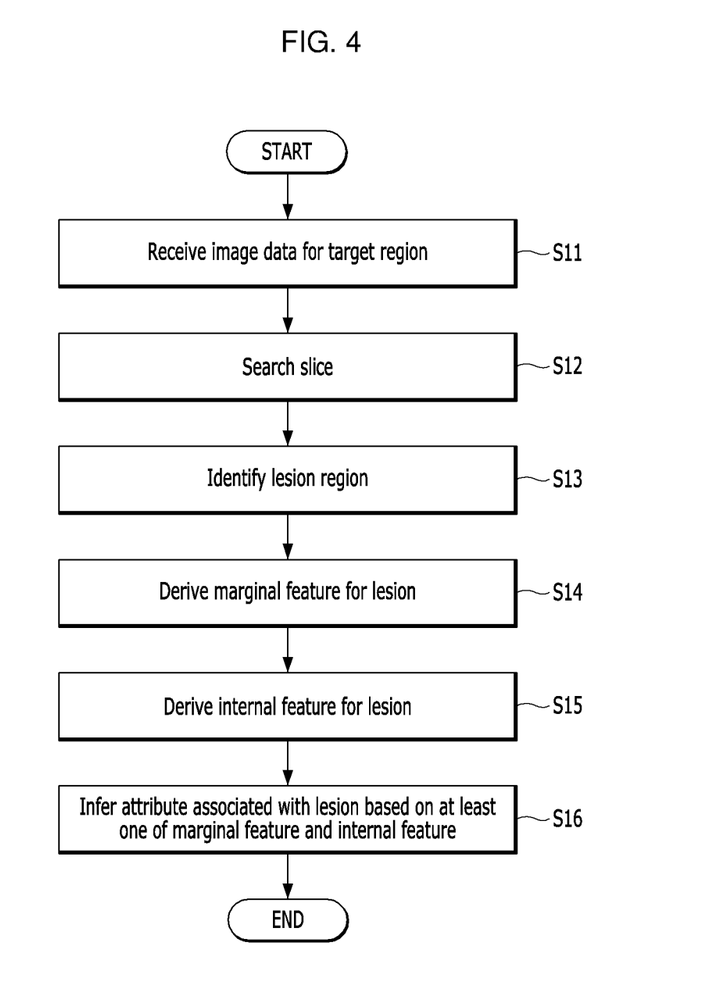
FIG. 4 is an operational flowchart of a method for lesion analysis based on a marginal feature according to an embodiment of the present disclosure.

FIG. 4 is an operational flowchart of a method for lesion analysis based on a marginal feature according to an embodiment of the present disclosure.

The method for lesion analysis based on the marginal feature illustrated in FIG. 4 may be performed by the lesion analysis apparatus 100 described above. Accordingly, although omitted below, the contents described with respect to the lesion analysis apparatus 100 may be applied in the same manner as the description of the method for lesion analysis based on the marginal feature.

Referring to FIG. 4, in step S11, the input reception unit 110 may receive image data for a target region.

Next, in step S12, the ROI detection unit 120 may search a slice in which a lesion region is better identified among a plurality of 2D slices for 3D computed tomography (CT) data received as the image data.

Next, in step S13, the ROI detection unit 120 may identify the lesion region from the image data. That is, in step S13, the ROI detection unit 120 may identify the lesion region from the slice determined as the lesion region is best identified among the plurality of 2D slices.

Next, in step S14, the marginal feature calculation unit 130 may derive a marginal feature for the lesion based on intensity information of the identified lesion region.

Next, in step S15, the internal feature calculation unit 140 may derive a texture feature for the lesion inside based on intensity information inside the identified lesion region.

Next, in step S16, the determination unit 150 may infer an attribute associated with the lesion based on at least one of the derived marginal feature and texture feature.

Specifically, in step S16, the determination unit 150 may infer invasiveness associated with the lesion as an attribute by considering an aspect in which a CDF derived as the marginal feature is rapidly changed or gently changed.

Further, in step S16, the determination unit 150 may classify a type of lesion based on the attribute (e.g., invasiveness, etc.) of the lesion inferred in step S15. Specifically, when a target region is lung and a lesion to be analyzed corresponds to lung adenocarcinoma, in step S15, the determination unit 150 may operate to classify the type of lesion as adenocarcinoma in situ, minimally invasive adenocarcinoma, and invasive adenocarcinoma based on the invasiveness of the lung region lesion.

In the above description, steps S11 to S16 may be further divided into additional steps or may be combined with less steps according to an embodiment of the present disclosure. In addition, some steps may be omitted if necessary, or the order between the steps may also be changed.

Figure 5:
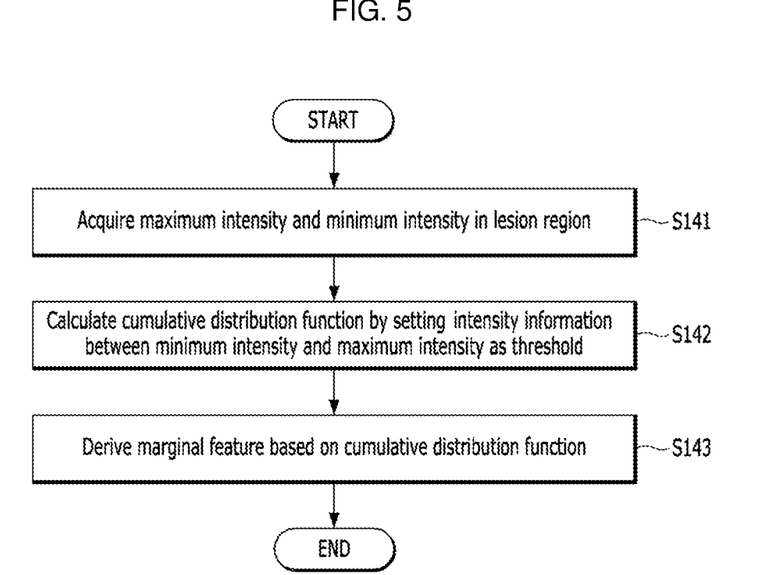
FIG. 5 is a detailed operational flowchart of a method for deriving a marginal feature according to an embodiment of the present disclosure.

FIG. 5 is a detailed operational flowchart of a method for deriving a marginal feature according to an embodiment of the present disclosure.

The method for lesion analysis based on the marginal feature illustrated in FIG. 5 may be performed by the lesion analysis apparatus 100 described above. Accordingly, although omitted below, the contents described with respect to the lesion analysis apparatus 100 may be applied in the same manner as the description of FIG. 5.

Referring to FIG. 5, in step S141, the CDF calculation unit 131 may acquire maximum intensity and minimum intensity in the lesion region identified in step S13.

Next, in step S142, the CDF calculation unit 131 may calculate a CDF for a lesion region by setting intensity information between the minimum intensity and the maximum intensity as a threshold.

Next, in step S143, the marginal feature calculation unit 133 may derive the marginal feature based on the derived CDF.

Specifically, in step S143, the marginal feature calculation unit 133 may derive an average, a standard deviation, skewness, and kurtosis of slope values of the CDF as the marginal feature based on the graph of the CDF acquired in step S142.

In the above description, steps S141 to S143 may be further divided into additional steps or may be combined with less steps according to an embodiment of the present disclosure. In addition, some steps may be omitted if necessary, or the order between the steps may also be changed.

The method for lesion analysis based on the marginal feature according to the embodiment of the present disclosure may be implemented in a form of program instructions which may be performed through various computer means to be recorded in a computer readable medium. The computer readable medium may include program instructions, a data file, a data structure, and the like alone or in combination. The program instructions recorded in the medium may be specially designed and configured for the present disclosure, or may be publicly known to and used by those skilled in a computer software field. Examples of the computer readable medium include magnetic media, such as a hard disk, a floppy disk, and a magnetic tape, optical media such as a CD-ROM and a DVD, magneto-optical media such as a floptical disk, and hardware devices such as a ROM, a RAM, and a flash memory, which are specially configured to store and execute the program command. Examples of the program instructions include high-level language codes executable by a computer by using an interpreter and the like, as well as machine language codes created by a compiler. The hardware device may be configured to be operated with one or more software modules in order to perform the operation of the present disclosure and vice versa.

Further, the aforementioned method for lesion analysis based on the marginal feature may be implemented even in a form of computer programs or applications to be executed by a computer, which are stored in the recording medium.

The aforementioned description of the present disclosure is to be exemplified, and it may be understood by those skilled in the art that the technical spirit or required features of the present disclosure may be easily modified in other detailed forms without changing. Therefore, it should be appreciated that the aforementioned embodiments described above are illustrative in all aspects and are not restricted. For example, respective components described as single types may be distributed and implemented, and similarly, components described to be distributed may also be implemented in a coupled form.

The scope of the present disclosure is represented by claims to be described below rather than the detailed description, and it is to be interpreted that the meaning and scope of the claims and all the changes or modified forms derived from the equivalents thereof come within the scope of the present disclosure.

What is claimed is:

1. A method for lesion analysis based on a marginal feature comprising:
   receiving image data for a target region;
   identifying a lesion region from the image data;
   deriving a marginal feature for a lesion based on intensity information of the identified lesion region; and
   inferring an attribute associated with the lesion based on the marginal feature,
   wherein the deriving of the marginal feature comprises:
   acquiring maximum intensity and minimum intensity in the identified lesion region;
   calculating a cumulative distribution function for the lesion region by setting intensity information between the minimum intensity and the maximum intensity as a threshold; and
   deriving the marginal feature based on the cumulative distribution function, and
   wherein the inferring of the attribute is to infer invasiveness associated with the lesion as the attribute based on the marginal feature by reflecting an aspect that the cumulative distribution function is rapidly changed or gently changed.

2. The method for lesion analysis of claim 1, wherein the deriving of the marginal feature based on the cumulative distribution function is to derive an average, a standard deviation, skewness, and kurtosis of slope values of the cumulative distribution function as the marginal feature based on the graph of the cumulative distribution function.

3. The method for lesion analysis of claim 1, further comprising:
   classifying a type of the lesion based on the inferred attribute.

4. The method for lesion analysis of claim 3, wherein the target region is lung and the type of the lesion is classified based on invasiveness of a lung region lesion.

5. The method for lesion analysis of claim 4, wherein the type of the lesion includes adenocarcinoma in situ, minimally invasive adenocarcinoma, and invasive adenocarcinoma.

6. The method for lesion analysis of claim 1, further comprising:
   after the identifying of the lesion region,
   deriving a texture feature for an interior of a lesion based on the intensity information inside the lesion region,
   wherein the inferring of the attribute is to infer an attribute associated with a lesion by considering both the marginal feature and the texture feature.

7. The method for lesion analysis of claim 6, further comprising:
   the image data is 3D computed tomography (CT) data,
   after the receiving of the image data,
   searching a slice in which the lesion region is best identified among a plurality of 2D slices for the 3D CT data.

8. An apparatus for lesion analysis based on a marginal feature comprising:
   an image receptor for receiving image data for a target region;
   an ROI detector for identifying a lesion region from the image data;
   a marginal feature calculator for deriving a marginal feature for a lesion based on intensity information of the identified lesion region; and a determinator for inferring an attribute associated with the lesion based on the marginal feature, wherein the marginal feature calculator comprises:

a CDF calculator for acquiring maximum intensity and minimum intensity in the identified lesion region and calculating a cumulative distribution function for the lesion region by setting intensity information between the minimum intensity and the maximum intensity as a threshold; and a marginal feature calculator for deriving the marginal feature based on the cumulative distribution function, and wherein the determinator infers invasiveness associated with the lesion as the attribute based on the marginal feature by reflecting an aspect that the cumulative distribution function is rapidly changed or gently changed.

9. The apparatus for lesion analysis of claim 8, further comprising:

an internal feature calculator for deriving a texture feature for an interior of a lesion based on the intensity information inside the lesion region, wherein the determinator infers the attribute associated with the lesion by considering both the marginal feature and the texture feature.

10. The apparatus for lesion analysis of claim 9, wherein the target region is lung, and the determinator classifies a type of the lesion based on the inferred attribute and classifies the type of the lesion based on invasiveness of a lung region lesion.

11. The apparatus of claim 8, wherein the ROI detector is configured to identify the lesion region based on identifying a ground glass opacity feature in the image data.

12. The apparatus of claim 8, wherein the ROI detector is configured to identify the lesion region based on a set of pixels or a set of voxels exceeding a threshold intensity value from the image data.

13. A non-transitory computer readable recording medium which records programs for executing the method of claim 1 in a computer.

* * * * *